(12) United States Patent
Hammons et al.

(10) Patent No.: US 7,910,195 B2
(45) Date of Patent: Mar. 22, 2011

(54) ABSORBENT ARTICLE WITH LOTION-CONTAINING TOPSHEET

(75) Inventors: John Lee Hammons, Fairfield Township, OH (US); John Richard Noel, Symmes Township, OH (US); Raphael Warren, Amberly Village, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/778,478

(22) Filed: May 12, 2010

(65) Prior Publication Data

US 2010/0222759 A1    Sep. 2, 2010

Related U.S. Application Data

(63) Continuation of application No. 11/157,770, filed on Jun. 21, 2005, now Pat. No. 7,732,657, which is a continuation-in-part of application No. 10/737,306, filed on Dec. 16, 2003, now Pat. No. 7,553,532, and a continuation-in-part of application No. 10/737,430, filed on Dec. 16, 2003, now Pat. No. 7,410,683.

(60) Provisional application No. 60/581,483, filed on Jun. 21, 2004.

(51) Int. Cl.
*B32B 3/10* (2006.01)
*B32B 3/02* (2006.01)

(52) U.S. Cl. .............. 428/133; 428/89; 428/91; 428/95; 428/137; 428/172; 604/358

(58) Field of Classification Search .................... 428/89, 428/95, 91, 133, 137, 172; 604/358
See application file for complete search history.

(56) References Cited

U.S. PATENT DOCUMENTS

| | | | |
|---|---|---|---|
| 2,068,456 A | 1/1937 | Hooper |
| 2,275,425 A | 3/1942 | Grabec |
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Griswold et al. |
| 3,081,512 A | 3/1963 | Griswold |

(Continued)

FOREIGN PATENT DOCUMENTS

EP    0 509 012 B1    7/1995

(Continued)

OTHER PUBLICATIONS

Office Action for U.S. Appl. No. 11/650,821 dated Oct. 16, 2007; Hoying et al.; filed Jan. 8, 2007.

(Continued)

*Primary Examiner* — Norca L Torres-Velazquez
(74) *Attorney, Agent, or Firm* — Andrew J. Hagerty

(57) ABSTRACT

A sanitary napkin comprising a topsheet having a body-facing side and comprising a plurality of discrete tufts of fibrous material. The topsheet has a lotion composition applied to at least a portion of the body-facing side thereof. An absorbent core is in fluid communication with the topsheet, the absorbent core having an average thickness of less than about 10 mm, and a free absorbent capacity of from about 4 to about 125 grams per gram.

10 Claims, 7 Drawing Sheets

U.S. PATENT DOCUMENTS

| | | | |
|---|---|---|---|
| 3,137,893 A | 6/1964 | Gelpke | |
| 3,355,974 A | 12/1967 | Carmichael | |
| 3,511,740 A | 5/1970 | Sanders | |
| 3,542,634 A | 11/1970 | Such et al. | |
| 3,566,726 A | 3/1971 | Politis | |
| 3,579,763 A | 5/1971 | Sommer | |
| 3,681,182 A | 8/1972 | Kalwaites | |
| 3,681,183 A | 8/1972 | Kalwaites | |
| 3,684,284 A | 8/1972 | Tranfield | |
| 3,695,270 A | 10/1972 | Dostal | |
| 3,718,059 A | 2/1973 | Clayton | |
| 3,760,671 A | 9/1973 | Jenkins | |
| 3,881,987 A | 5/1975 | Benz | |
| 3,949,127 A | 4/1976 | Ostermeier et al. | |
| 3,965,906 A | 6/1976 | Karami | |
| 4,035,881 A | 7/1977 | Zocher | |
| 4,042,453 A | 8/1977 | Conway | |
| 4,135,021 A | 1/1979 | Patchell et al. | |
| 4,276,336 A | 6/1981 | Sabee | |
| 4,379,799 A | 4/1983 | Holmes | |
| 4,397,644 A | 8/1983 | Matthews et al. | |
| 4,465,726 A | 8/1984 | Holmes | |
| 4,469,734 A | 9/1984 | Minto et al. | |
| 4,588,630 A | 5/1986 | Shimalla | |
| 4,741,941 A | 5/1988 | Englebert et al. | |
| 4,758,297 A | 7/1988 | Calligarich | |
| 4,781,962 A | 11/1988 | Zamarripa et al. | |
| 4,798,604 A | 1/1989 | Carter | |
| 4,820,294 A | 4/1989 | Morris | |
| 4,840,829 A | 6/1989 | Suzuki et al. | |
| 4,859,519 A | 8/1989 | Cabe, Jr. et al. | |
| 4,886,632 A | 12/1989 | Van Iten et al. | |
| 4,935,087 A | 6/1990 | Gilman | |
| 4,953,270 A | 9/1990 | Gilpatrick | |
| 5,019,062 A | 5/1991 | Ryan et al. | |
| 5,062,418 A | 11/1991 | Dyer | |
| 5,144,730 A | 9/1992 | Dilo | |
| 5,165,979 A | 11/1992 | Watkins et al. | |
| 5,171,238 A | 12/1992 | Kajander | |
| 5,180,620 A | 1/1993 | Mende | |
| 5,188,625 A | 2/1993 | Van Iten et al. | |
| 5,223,319 A | 6/1993 | Cotton et al. | |
| 5,242,632 A | 9/1993 | Mende | |
| 5,268,224 A | 12/1993 | DesMarais et al. | |
| 5,382,245 A | 1/1995 | Thompson | |
| 5,383,870 A | 1/1995 | Takai et al. | |
| 5,387,209 A | 2/1995 | Yamamoto et al. | |
| 5,414,914 A | 5/1995 | Suzuki et al. | |
| 5,415,640 A | 5/1995 | Kirby et al. | |
| 5,429,854 A | 7/1995 | Currie et al. | |
| 5,437,653 A | 8/1995 | Gilman et al. | |
| 5,470,326 A | 11/1995 | Dabi et al. | |
| 5,508,080 A | 4/1996 | Sorimachi et al. | |
| 5,518,801 A | 5/1996 | Chappell et al. | |
| 5,533,991 A | 7/1996 | Kirby et al. | |
| 5,554,145 A | 9/1996 | Roe | |
| 5,560,794 A | 10/1996 | Currie et al. | |
| 5,567,501 A | 10/1996 | Srinivasan et al. | |
| D375,844 S | 11/1996 | Edwards et al. | |
| 5,573,719 A | 11/1996 | Fitting | |
| 5,575,874 A | 11/1996 | Griesbach, III et al. | |
| 5,580,418 A | 12/1996 | Alikhan | |
| 5,599,420 A | 2/1997 | Yeo et al. | |
| 5,624,427 A | 4/1997 | Dreier et al. | |
| 5,624,729 A | 4/1997 | Cohen et al. | |
| 5,626,571 A | 5/1997 | Young et al. | |
| 5,628,097 A | 5/1997 | Benson et al. | |
| 5,635,191 A | 6/1997 | Roe et al. | |
| 5,643,588 A | 7/1997 | Roe et al. | |
| 5,648,142 A | 7/1997 | Phillips | |
| 5,656,119 A | 8/1997 | Srinivasan et al. | |
| 5,658,639 A | 8/1997 | Curro et al. | |
| 5,667,619 A | 9/1997 | Alikhan | |
| 5,667,625 A | 9/1997 | Alikhan | |
| 5,691,035 A | 11/1997 | Chappell et al. | |
| 5,700,255 A | 12/1997 | Curro | |
| 5,704,101 A | 1/1998 | Majors et al. | |
| 5,709,829 A | 1/1998 | Giacometti | |
| 5,714,107 A | 2/1998 | Levy et al. | |
| 5,723,087 A | 3/1998 | Chappell et al. | |
| 5,743,776 A | 4/1998 | Igaue | |
| 5,804,021 A | 9/1998 | Abuto et al. | |
| 5,814,389 A | 9/1998 | Giacometti | |
| 5,817,394 A | 10/1998 | Alikhan et al. | |
| 5,841,107 A | 11/1998 | Riva | |
| 5,858,504 A | 1/1999 | Fitting | |
| 5,879,494 A | 3/1999 | Hoff et al. | |
| 5,891,544 A | 4/1999 | Chappell et al. | |
| 5,895,623 A | 4/1999 | Trokhan et al. | |
| 5,914,084 A | 6/1999 | Benson et al. | |
| 5,916,661 A | 6/1999 | Benson et al. | |
| 5,919,177 A | 7/1999 | Georger et al. | |
| 5,925,026 A | 7/1999 | Arteman et al. | |
| 5,932,316 A * | 8/1999 | Cree et al. ...................... 428/182 |
| 5,964,742 A | 10/1999 | McCormack et al. | |
| 5,968,025 A | 10/1999 | Roe et al. | |
| 5,968,029 A | 10/1999 | Chappell | |
| 5,986,167 A | 11/1999 | Arteman et al. | |
| 5,993,432 A | 11/1999 | Lodge et al. | |
| 6,007,468 A | 12/1999 | Giacometti | |
| 6,025,050 A | 2/2000 | Srinivasan et al. | |
| 6,027,483 A | 2/2000 | Chappell et al. | |
| 6,039,555 A | 3/2000 | Tsuji et al. | |
| 6,096,016 A | 8/2000 | Tsuji et al. | |
| 6,107,537 A * | 8/2000 | Elder et al. ...................... 604/364 |
| 6,114,263 A | 9/2000 | Benson et al. | |
| 6,117,524 A | 9/2000 | Hisanaka et al. | |
| 6,118,041 A | 9/2000 | Roe et al. | |
| 6,120,718 A | 9/2000 | Kotek et al. | |
| 6,129,801 A | 10/2000 | Benson et al. | |
| 6,155,083 A | 12/2000 | Goeser et al. | |
| 6,168,849 B1 | 1/2001 | Braverman et al. | |
| 6,176,954 B1 | 1/2001 | Tsuji et al. | |
| 6,247,914 B1 | 6/2001 | Lindquist et al. | |
| D444,631 S | 7/2001 | Woodbridge et al. | |
| 6,264,872 B1 | 7/2001 | Majors et al. | |
| 6,287,407 B1 | 9/2001 | Stein et al. | |
| 6,383,431 B1 | 5/2002 | Dobrin et al. | |
| 6,395,122 B1 | 5/2002 | Hisanaka et al. | |
| 6,395,211 B1 | 5/2002 | Dettmer et al. | |
| 6,398,895 B1 | 6/2002 | Stein et al. | |
| 6,410,823 B1 | 6/2002 | Daley et al. | |
| 6,417,426 B1 | 7/2002 | Takai et al. | |
| 6,420,625 B1 | 7/2002 | Jones et al. | |
| 6,423,884 B1 | 7/2002 | Oehmen | |
| 6,426,444 B2 | 7/2002 | Roe et al. | |
| 6,451,718 B1 | 9/2002 | Yamada et al. | |
| 6,452,064 B1 | 9/2002 | Thoren et al. | |
| 6,458,447 B1 | 10/2002 | Cabell | |
| 6,479,130 B1 | 11/2002 | Takai et al. | |
| D466,702 S | 12/2002 | Carlson et al. | |
| 6,506,329 B1 | 1/2003 | Curro et al. | |
| 6,537,936 B1 | 3/2003 | Busam et al. | |
| 6,586,652 B1 | 7/2003 | Roe et al. | |
| 6,620,485 B1 | 9/2003 | Benson et al. | |
| 6,627,787 B1 | 9/2003 | Roe et al. | |
| 6,632,504 B1 | 10/2003 | Gillespie et al. | |
| D481,872 S | 11/2003 | Hennel et al. | |
| 6,647,549 B2 | 11/2003 | McDevitt et al. | |
| 6,669,878 B2 | 12/2003 | Yamada et al. | |
| 6,716,498 B2 | 4/2004 | Curro et al. | |
| 6,726,870 B1 | 4/2004 | Benson et al. | |
| 6,736,916 B2 | 5/2004 | Steinke et al. | |
| 6,794,626 B2 | 9/2004 | Kiermeier et al. | |
| 6,808,791 B2 | 10/2004 | Curro et al. | |
| 6,818,802 B2 | 11/2004 | Takai et al. | |
| 6,825,393 B2 | 11/2004 | Roe et al. | |
| 6,830,800 B2 | 12/2004 | Curro et al. | |
| 6,837,956 B2 | 1/2005 | Cowell et al. | |
| 6,855,220 B2 | 2/2005 | Wildeman | |
| 6,861,571 B1 | 3/2005 | Roe et al. | |
| 6,863,960 B2 | 3/2005 | Curro et al. | |
| 6,872,274 B2 | 3/2005 | Kauschke et al. | |
| 6,884,494 B1 | 4/2005 | Curro et al. | |
| 7,005,558 B1 | 2/2006 | Johansson et al. | |
| 7,037,569 B2 | 5/2006 | Curro et al. | |
| 2002/0039867 A1 | 4/2002 | Curro et al. | |

| | | |
|---|---|---|
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki |
| 2003/0021951 A1 | 1/2003 | Desai et al. |
| 2003/0028165 A1 | 2/2003 | Curro et al. |
| 2003/0082219 A1 | 5/2003 | Warren et al. |
| 2003/0085213 A1 | 5/2003 | Burckhardt et al. |
| 2003/0191442 A1 | 10/2003 | Bewick-Sonntag |
| 2003/0191443 A1 | 10/2003 | Taylor |
| 2003/0206943 A1 | 11/2003 | Hammons et al. |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0170589 A1 | 9/2004 | Gatto |
| 2004/0193126 A1 | 9/2004 | Roe et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0064136 A1 | 3/2005 | Turner et al. |
| 2005/0096614 A1 | 5/2005 | Perez et al. |
| 2005/0123726 A1 | 6/2005 | Broering et al. |
| 2005/0129651 A1 | 6/2005 | Gatto et al. |
| 2005/0154362 A1 | 7/2005 | Warren et al. |
| 2005/0208112 A1 | 9/2005 | Roe et al. |
| 2005/0208113 A1 | 9/2005 | Roe et al. |
| 2006/0087053 A1 | 4/2006 | O'Donnell et al. |
| 2006/0148962 A1 | 7/2006 | Bersted et al. |

FOREIGN PATENT DOCUMENTS

| | | |
|---|---|---|
| EP | 0 955 159 A1 | 11/1999 |
| EP | 0 963 747 A1 | 12/1999 |
| EP | 1 004 412 A1 | 5/2000 |
| FR | 2713083 * | 6/1995 |
| WO | WO 95/15138 | 6/1995 |
| WO | WO 02/100632 A1 | 12/2002 |
| WO | WO 2005/011936 A1 | 2/2005 |

OTHER PUBLICATIONS

Office Action for U.S. Appl. No. 11/650,821 dated Oct. 8, 2008; Hoying et al.; filed Jan. 8, 2007.
Office Action for U.S. Appl. No. 11/650,821 dated Apr. 23, 2008; Hoying et al.; filed Jan. 8, 2007.
Office Action for U.S. Appl. No. 11/650,821 dated Mar. 16, 2009; Hoying et al.; filed Jan. 8, 2007.
Notice of Allowance for U.S. Appl. No. 11/650,821 dated Nov. 9. 2009; Hoying et al.; filed Jan. 8, 2007.
Notice of Allowance for U.S. Appl. No. 10/737,307 dated Sep. 28, 2006; Hoying et al.; filed Dec. 16, 2003.
Office Action for U.S. Appl. No. 10/737,307 dated May 31, 2006; Hoying et al.; filed Dec. 16, 2003.
Office Action for U.S. Appl. No. 10/737,307 dated Oct. 7, 2005; Hoying et al.; filed Dec. 16, 2003.
Notice of Allowance for U.S. Appl. No. 10/980,219 dated May 23, 2007; Broering et al.; filed Nov. 3, 2004.
Office Action for U.S. Appl. No. 10/980,219 dated May 23, 2007; Broering et al.; filed Nov. 3, 2004.
Office Action for U.S. Appl. No. 10/980,219 dated Sep. 11, 2006; Broering et al.; filed Nov. 3, 2004.
Office Action for U.S. Appl. No. 12/370,850 dated Jul. 8, 2009; Turner et al.; filed Feb. 13, 2009.
Office Action for U.S. Appl. No. 12/370,850 dated Dec. 29, 2009; Turner et al.; filed Feb. 13, 2009.
Notice of Allowance for U.S. Appl. No. 12/370,850 dated Mar. 9, 2010; Turner et al.; filed Feb. 13, 2009.
Notice of Allowance for U.S. Appl. No. 10/737,430 dated Mar. 18, 2008; Curro et al.; filed Dec. 16, 2003.
Notice of Allowance for U.S. Appl. No. 10/737,430 dated Oct. 29, 2007; Curro et al.; filed Dec. 16, 2003.
Office Action for U.S. Appl. No. 10/737,430 dated Jul. 16, 2007; Curro et al.; filed Dec. 16, 2003.
Office Action for U.S. Appl. No. 10/737,430 dated Jan. 25, 2007; Curro et al.; filed Dec. 16, 2003.
Office Action for U.S. Appl. No. 10/737,430 dated Aug. 8, 2006; Curro et al.; filed Dec. 16, 2003.
Office Action for U.S. Appl. No. 10/737,430 dated Feb. 3, 2006; Curro et al.; filed Dec. 16, 2003.
Office Action for U.S. Appl. No. 10/737,430 dated Aug. 24, 2005; Curro et al.; filed Dec. 16, 2003.
Notice of Allowance for U.S. Appl. No. 10/737,306 dated Nov. 29, 2007; Gray et al.; filed Mar. 28, 2003.
Office Action for U.S. Appl. No. 10/737,306 dated Jun. 12, 2008; Gray et al.; filed Mar. 28, 2003.
Office Action for U.S. Appl. No. 10/737,306 dated Jul. 16, 2007; Gray et al.; filed Mar. 28, 2003.
Office Action for U.S. Appl. No. 10/737,306 dated Jan. 26, 2007; Gray et al.; filed Mar. 28, 2003.
Office Action for U.S. Appl. No. 10/737,306 dated Aug. 9, 2006; Gray et al.; filed Mar. 28, 2003.
Office Action for U.S. Appl. No. 10/737,306 dated Aug. 24, 2005; Gray et al.; filed Mar. 28, 2003.
Office Action for U.S. Appl. No. 10/737,306 dated Feb. 3, 2006; Gray et al.; filed Mar. 28, 2003.
Office Action for U.S. Appl. No. 11/158,165 dated May 16, 2008; Turner et al.; filed Jun. 21, 2005.
Office Action for U.S. Appl. No. 11/158,165 dated Dec. 7, 2007; Turner et al.; filed Jun. 21, 2005.
Office Action for U.S. Appl. No. 11/158,165 dated Jul. 3, 2007; Turner et al; filed Jun. 21, 2005.
Office Action for U.S. Appl. No. 11/157,770 dated Oct. 1, 2007; Hammons et al.; filed Jun, 21, 2005.
Office Action for U.S. Appl. No. 11/157,770 dated Jun, 2, 2008; Hammons et al.; filed Jun. 21, 2005.
Office Action for U.S. Appl. No. 11/157,770 dated Apr. 28, 2009; Hammons et al.; filed Jun. 21, 2005.
Office Action for U.S. Appl. No. 11/157,770 dated Nov. 10, 2009; Hammons et al.; filed Jun. 21, 2005.
Notice of Allowance for U.S. Appl. No. 11/157,770 dated Jan. 26, 2010; Hammons et al.; filed Jun. 21, 2005.
Office Action for U.S. Appl. No. 11/156,020 dated Jul. 8, 2009; Curro et al.; filed Jun. 17, 2005.
Office Action for U.S. Appl. No. 11/156,020 dated Dec. 24, 2008; Curro et al.; filed Jun. 17, 2005.
Office Action for U.S. Appl. No. 11/156,020 dated Jul. 10, 2008; Curro et al.; filed Jun. 17, 2005.
Office Action for U.S. Appl. No. 11/156,020 dated Nov. 27, 2007; Curro et al.; filed Jun. 17, 2005.
Office Action for U.S. Appl. No. 11/156,020 dated Jun. 20, 2007; Curro et al.; filed Jun. 17, 2005.
Office Action for U.S. Appl. No. 11/156,020 dated Jan. 12, 2007; Curro et al.; filed Jun. 17, 2005.
Notice of Allowance for U.S. Appl. No. 11/156,020 dated Nov. 30, 2009; Curro et al.; filed Jun. 17, 2005.
Office Action for U.S. Appl. No. 11/155,805 dated Feb. 19, 2010; Curro et al.; filed Jun. 17, 2005.
Examiner's Answer for U.S. Appl. No. 11/155,805 dated Aug. 6, 2009; Curro et al.; filed Jun. 17, 2005.
Office Action for U.S. Appl. No. 11/155,805 dated Nov. 13, 2009; Curro et al.; filed Jun. 17, 2005.
Office Action for U.S. Appl. No. 11/155,805 dated Oct. 30, 2008; Curro et al.; filed Jun. 17, 2005.
Office Action for U.S. Appl. No. 11/155,805 dated May 16, 2008; Curro et al.; filed Jun. 17, 2005.
Office Action for U.S. Appl. No. 11/155,805 dated Nov. 27, 2007; Curro et al.; filed Jun. 17, 2005.
Office Action for U.S. Appl. No. 11/155,805 dated Jun. 19, 2007; Curro et al.; filed Jun. 17, 2005.
Office Action for U.S. Appl. No. 10/737,235 dated May 6, 2009; Hoying et al.; filed Dec. 16, 2003.
Office Action for U.S. Appl. No. 10/737,235 dated Nov. 25, 2008; Hoying et al.; filed Dec. 16, 2003.

Notice of Allowance for U.S. Appl. No. 10/737,235 dated Oct. 6, 2009; Hoying et al.; filed Dec. 16, 2003.
Office Action for U.S. Appl. No. 10/737,235 dated Jun. 12, 2008; Hoying et al.; filed Dec. 16, 2003.
Office Action for U.S. Appl. No. 10/737,235 dated Dec. 12, 2007; Hoying et al.; filed Dec. 16, 2003.
Office Action for U.S. Appl. No. 10/737,235 dated Jul. 26, 2007; Hoying et al.; filed Dec. 16, 2003.
Office Action for U.S. Appl. No. 10/737,235 dated Feb. 6, 2007; Hoying et al.; filed Dec. 16, 2003.
Office Action for U.S. Appl. No. 10/737,235 dated Aug. 8, 2006; Hoying et al.; filed Dec. 16, 2003.
Office Action for U.S. Appl. No. 10/737,235 dated Feb. 3, 2006; Hoying et al.; filed Dec. 16, 2003.
Office Action for U.S. Appl. No. 10/737,235 dated Aug. 24, 2005; Hoying et al.; filed Dec. 16, 2003.
Office Action for U.S. Appl. No. 12/021,369 dated Jun. 25, 2009; Curro et al.; filed Jan. 29, 2008.
Office Action for U.S. Appl. No. 12/021,369 dated Dec. 29, 2009; Curro et al.; filed Jan. 29, 2008.
Notice of Allowance for U.S. Appl. No. 12/021,369 dated Feb. 19, 2010; Curro et al.; filed Jan. 29, 2008.
Office Action for U.S. Appl. No. 11/129,877 dated Mar. 30, 2007; Cabell; filed May 16, 2005.
Office Action for U.S. Appl. No. 11/129,877 dated Oct. 2, 2007; Cabell; filed May 16, 2005.
Office Action for U.S. Appl. No. 11/129,877 dated Jan. 23, 2008; Cabell; filed May 16, 2005.
Office Action for U.S. Appl. No. 11/129,877 dated Jun. 12, 2008; Cabell; filed May 16, 2005.
PCT International Search Report dated Nov. 18, 2005.

* cited by examiner

ABSORBENT ARTICLE WITH LOTION-CONTAINING TOPSHEET

CROSS REFERENCE TO RELATED APPLICATIONS

This application is a continuation of U.S. application Ser. No. 11/157,770 filed Jun. 21, 2005 now U.S. Pat. No. 7,732, 657, which claims the benefit of U.S. Provisional Application 60/581,483, filed Jun. 21, 2004, and which is a continuation-in-part of U.S. application Ser. No. 10/737,306, filed Dec. 16, 2003 now U.S. Pat. No. 7,553,532, and a continuation-in-part of U.S. application Ser. No. 10/737,430, filed Dec. 16, 2003, now U.S. Pat. No. 7,410,683.

FIELD OF INVENTION

This invention relates to fibrous webs such as nonwoven webs suitable for use as a topsheet in a disposable absorbent article. In particular, this invention relates to fibrous is webs treated by mechanical formation to have increased softness or bulk properties, and having a lotion applied thereto.

BACKGROUND OF THE INVENTION

Disposable absorbent articles such as baby diapers, adult incontinence products, sanitary napkins, pantiliners, hemorrhoid treatment pads, bandages, and the like are well known in the art. Such articles generally have a fluid permeable topsheet, and fluid impermeable backsheet, and an absorbent core sandwiched between the topsheet and the backsheet to absorb and contain body fluid exudates.

In some applications of disposable absorbent articles, such as sanitary napkins and pantiliners, it is desirable to not only absorb body fluids, but to minimize fluid on the body of the wearer. Fluid on the body can be minimized by ensuring that the fluid enters the absorbent article, and does not come back out, such as by being pressed or squeezed out during the normal course of wearing the absorbent article, i.e., by sitting or walkin. While much work has been done in to minimize rewet to the body, there remains a need for a disposable absorbent article that helps keep the users body clean and dry.

Accordingly, there is a disposable absorbent article that helps provide for a clean body benefit in the area of sanitary napkins and pantiliners.

Additionally, there is a need for a method for relatively inexpensively making a disposable absorbent article that helps provide for a clean body benefit in the area of sanitary napkins and pantiliners.

SUMMARY OF THE INVENTION

A sanitary napkin comprising a topsheet having a body-facing side and comprising a plurality of discrete tufts of fibrous material is disclosed. The topsheet has a lotion composition applied to at least a portion of the body-facing side thereof. An absorbent core is in fluid communication with the topsheet, the absorbent core having an average thickness of less than about 10 mm, and a free absorbent capacity of from about 4 to about 125 grams per gram.

DETAILED DESCRIPTION OF THE INVENTION

Figure 1:
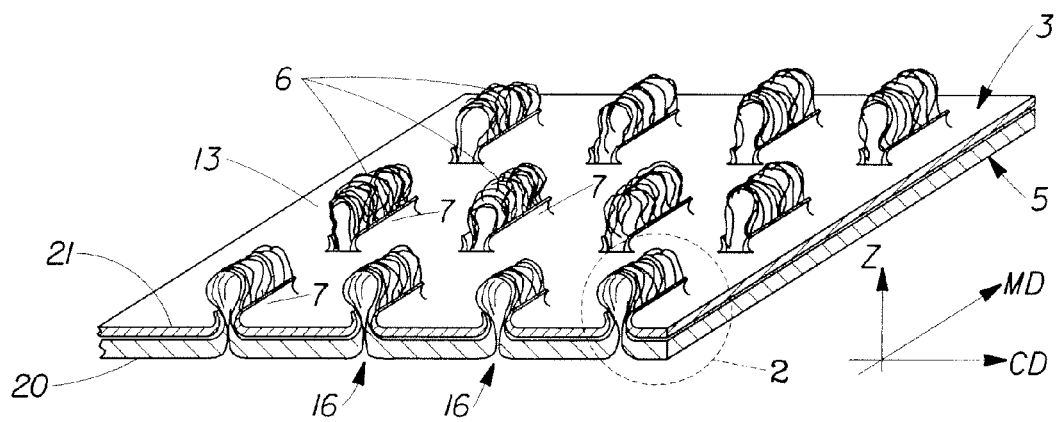
FIG. 1 is a perspective view of a web of the present invention.

The present invention can be utilized in any of known disposable absorbent products. In a preferred embodiment, however, the present invention comprises a sanitary napkin intended to be used as a menstrual pad. The sanitary napkin of the present invention comprises at least three components: a topsheet, a lotion applied to the topsheet, and an absorbent core in fluid communication with the topsheet. It has been unexpectedly found that, by using the combination of materials disclosed below, a sanitary napkin of the present invention can provide for a desirable clean body benefit. Specifically, the sanitary napkin of the present invention provides for better fluid acquisition and retention, such that less fluid is left on the body of the wearer, or is squeezed back out of the product onto the body of the wearer.

It has been found that application of a semi-solid lotion material to the top surface of a sanitary napkin can modulate skin properties and conditions of the wearer. It is believed that this is due to the semi-solid lotion melting when the article is worn against the body, and subsequent transferring from the topsheet to the skin of the wearer. In a preferred embodiment, the lotion is a hydrophobic semi-solid lotion, which when applied to the top surface of a sanitary napkin, especially when the sanitary napkin has a hydrophobic surface, can confer a benefit of reducing rewet from the article to the wearer's body, resulting in a drier wearing experience.

In one embodiment, a hydrophobic semi-solid lotion is applied to an absorbent article having a hydrophobic topsheet surface. Because such a lotion can tend to negatively affect the acquisition of the fluid into the absorbent article, resulting in soiling of the wearer's body and/or garments, the lotion is preferably applied in non-continuous patterns, such as in stripes or bands. In another embodiment, a hydrophobic semi-solid lotion is applied to an absorbent article having a hydrophilic topsheet surface.

It has been found that a hydrophobic semi-solid lotion material disposed on the outer, lateral side areas of a sanitary napkin having a hydrophobic topsheet allows for good fluid acquisition, reduced rewet, and reduced residual fluid on the body and transfer to the wearer's body. For example, the lotion can be applied in longitudinal stripes or bands. In one embodiment, the lotion is applied in two 22 mm stripes of longitudinally oriented bands, separated by a gap of about 20 mm free of lotion in the center of the article. Without being bound by theory, it is believed that when used with the topsheet and the core of the present invention, this permits the benefit of reduced rewet while preserving acquisition because the lotion can transfer to the wearers body more efficiently, particularly when the wearer's body is in motion. A hydrophobic coating can help prevent menses from sticking to the body, for example. Further, the lotion can also transfer back to the topmost area of the article. This lotion coating of the previously is uncoated surface of the article appears not to compromise the functioning of the article's surface and underlying absorbent materials, as might be the case when the semi-solid is melted and then uniformly applied on the surface by spray or slot coat application.

When the lotion of the present invention is applied as described and worn by the user, it is surprisingly found that only a small amount of the semi-solid lotion material transferred to the non-applied areas of the topsheet lowers rewet, without negatively affecting fluid acquisition. For example, in one embodiment, lotion in the amount of about 7 grams per square meter (gsm) on the areas of the topsheet (e.g., the stripe) where it is applied is adequate for transferring sufficient amounts of lotion to the skin and hair of the wearer. In other embodiments, lotion can be added at a basis weight of from about 8-20 gsm, in one gsm increments. In one embodiment, the lotion can be applied only to the tips of tufts 6 by use of a kiss roll, or printing roll, or the like. Such a topsheet delivers skin care and fluid handling benefits regardless of the underlying absorbent core and other components of the sanitary napkin.

The following description will describe in order: a topsheet of the present invention, a lotion of the present invention, and an absorbent core of the present invention.

FIG. 1 shows a laminate web 1 suitable for use as a topsheet in the present invention, hereinafter referred to simply as web 1. Web 1 can comprise one layer, but in a preferred embodiment comprises at least two layers. The layers are referred to herein as generally planar, two-dimensional precursor webs, such as first precursor web 20 and second precursor web 21. Either precursor web can be a film, a nonwoven, but in a preferred embodiment, both precursor webs are nonwoven webs. Precursor webs 20 and 21 (and any additional webs) can be joined by adhesive, thermal bonding, ultrasonic bonding and the like, but are preferably joined without the use of adhesive or other forms of bonding. As disclosed below, the constituent precursor webs of web 1 can be joined by interlocking mechanical engagement resulting from the formation of tufts 6.

Web 1 has a first side 3 and a second side 5, the term "sides" being used in the common usage of generally planar two-dimensional webs, such as paper and films that have two sides when in a generally flat condition. Each precursor web 20 and 21 has a first surface 12 and 13, respectively, and a second surface 14 and 15, respectively (shown in FIG. 3). Web 1 has a machine direction (MD) and a cross machine direction (CD) as is commonly known in the art of web manufacture. Although the present invention can be practiced with polymer films and woven webs, in a preferred embodiment both precursor webs are nonwoven webs comprised of substantially randomly oriented fibers. By "substantially randomly oriented" is meant that, due to processing conditions of the precursor web, there may be a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD. In a preferred embodiment, first precursor web 20 is a relatively hydrophilic nonwoven web and second precursor web 21 is a nonwoven web is a relatively hydrophobic nonwoven web. For all nonwoven webs, the hydrophobicity or hydrophilicity can be achieved by use of fibers having the proper characteristics, or the precursor webs can be treated to have the desired characteristics.

Figure 3:
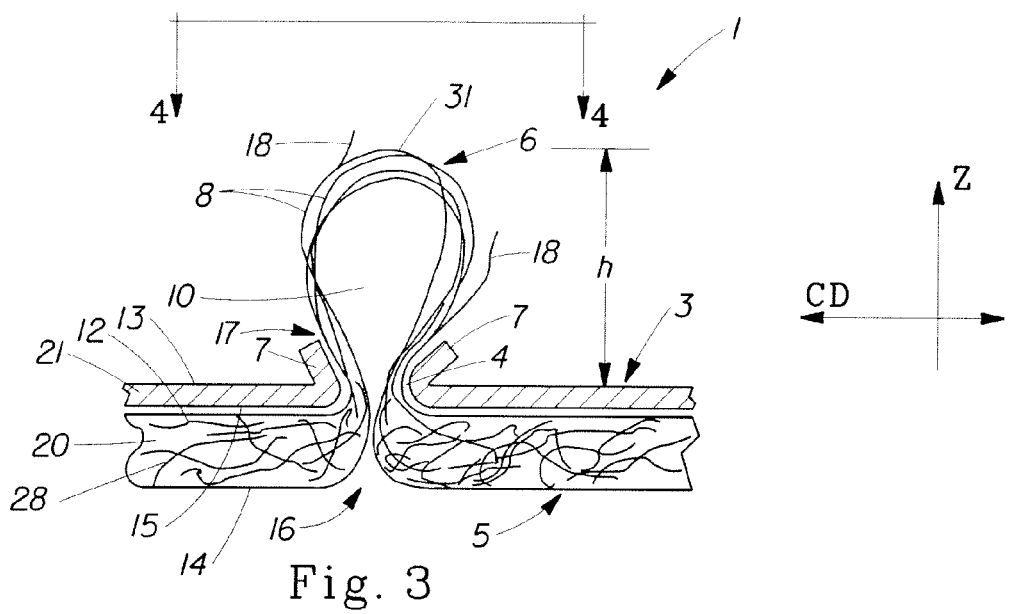
FIG. 3 is a cross-sectional view of section 3-3 of FIG. 2.

In one embodiment, first side 3 of web 1 is defined by exposed portions of the first surface 13 of second precursor web 21 and at least one, but preferably a plurality of, discrete tufts 6 which are integral extensions of the fibers of at least first precursor web 20 and preferably both precursor webs. As shown in FIG. 3, each tuft 6 can comprise a plurality of looped, aligned fibers 8 extending through second precursor web 21 and outwardly from the first surface 13 thereof. In another embodiment each tuft 6 can comprise a plurality of non-looped fibers 18 (as shown in FIG. 3) that extend outwardly from the first surface 13.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding. Fibers can be bicomponent, multicomponent, multiconstituent, and the like, as known in the art. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 10 gsm to 500 gsm.

The constituent fibers of nonwoven precursor web 20 or 21 can be comprised of polymers such as polyethylene, polypropylene, polyester, and blends thereof. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., capillary channel fibers), and can have major cross-sectional dimensions (e.g., diameter for round fibers) ranging from 0.1-500 microns. For example, one type of fibers suitable for the nonwoven web includes nanofibers. Nanofibers are described as fibers having a mean diameter of less than 1 micron. Nanofibers can comprise all of the fibers in a nonwoven web or a portion of the fibers in a nonwoven web. The constituent fibers of the nonwoven precursor web may also be a mixture of different fiber types, differing in such features as chemistry (e.g. PE and PP), components (mono- and bi-), denier (micro denier and >20 denier), shape (i.e. capillary and round) and the like. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, is between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie is arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multi-constituent fibers.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

As used herein, the term "integral" as in "integral extension" when used for the tufts 6 refers to fibers of the tufts 6 having originated from the fibers of the precursor webs. For example, fibers in tufts 6 can be integral with, i.e., originated in, first precursor web 20. Therefore, the looped fibers 8 and non-looped fibers 18 of tufts 6, can be s plastically deformed and extended fibers of the first precursor web 20, and are, therefore, integral with first precursor web 20. As used herein, "integral" is to be distinguished from fibers introduced to or added to a separate precursor web for the purpose of making tufts, as is commonly done in conventional carpet making, for example.

The number, spacing, and dimensions of tufts 6 can be varied to give varying texture to first side 3 of web 1. For example, if tufts 6 are sufficiently closely spaced the first side 3 of web 1 can have a terry cloth-like feel. Alternatively, tufts 6 can be arranged in patterns such as lines or filled shapes to create portions of a laminate web having greater texture, softness, bulk, absorbency or visual design appeal. For example, when tufts 6 are arranged in a pattern of a line or lines, the tufts can have the appearance of is stitching. Tufts 6 can also be arranged to form specific shapes, such as designs, words or logos. Such shapes can be used, for example, on laminates useful for hotel bath towels or robes which can have the name or logo of the hotel formed thereon. Likewise, the size dimensions, such as the height, length and width of individual tufts 6 can be varied. Single tufts can be as long as about 3 cm in length and can be made alone or dispersed among tufts of various sizes.

First precursor web 20 can be a fibrous woven or nonwoven web comprising fibers having sufficient elongation properties to have portions formed into tufts 6 as described more fully below. Tufts are formed by urging fibers out-of-plane in the Z-direction at discrete, localized, portions of first precursor web 20. The urging out-of-plane can be due to fiber displacement, i.e., the fiber is able to move relative to other fibers and be "pulled," so to speak, out-of-plane. More often, however, for most nonwoven first precursor webs 20, the urging out-of-plane is due to the fibers of tufts 6 having been at least partially plastically stretched and permanently deformed to form tufts 6. Therefore, in one embodiment, depending on the desired height of tufts 6, the constituent fibers of a nonwoven first precursor webs 20 can exhibit an elongation to break of at least about 5%, more preferably at least about 10%, more preferably at least about 25%, more preferably at least about 50%, and more preferably at least about 100%. Elongation to break can be determined by simple tensile testing, such as by use of Instron tensile testing equipment, and can generally be found on material data sheets from suppliers of such fibers or webs.

It can be appreciated that a suitable precursor webs should comprise fibers capable of experiencing sufficient plastic deformation and tensile elongation, or are capable of sufficient fiber mobility, such that looped fibers 8 are formed. However, it is recognized that a certain percentage of fibers urged out of the plane of the first surface 12 will not form a loop, but instead will break and form loose ends. Such fibers are referred to herein as "loose" fibers or "loose fiber ends" 18 as shown in FIG. 3. Loose fiber ends 18 are not necessarily undesirable for the present invention, and in some embodiments, most or all of the fibers of tufts 6 can be loose fiber ends 18. Loose fiber ends 18 can also be the result of forming tufts 6 from nonwoven webs consisting of, or containing, cut staple fibers. In such a case, some number of the staple fiber ends may protrude into the tuft 6, is depending upon such things as the number of staple fibers in the web, the staple fiber cut length, and the height of the tufts. In some instances, it may be desired to use a blend of fibers of different lengths in a precursor web or fibers of different lengths in different layers. This may be able to selectively separate the longer fibers from the shorter fibers. The longer fibers may predominately form the tuft 6 while the shorter fibers predominately remain in the portion of the web not forming the tuft 6. An exemplary mixture of fiber lengths can include fibers of approximately 2 to 8 centimeters for the longer fibers and less than about 1 centimeter for the shorter fibers.

First precursor web 20 can be a fibrous woven or nonwoven web comprising elastic or elastomeric fibers. Elastic or elastomeric fibers can be stretched at least about 50% and return to within 10% of their original dimension. Tufts 6 can be formed from elastic fibers if the fibers are simply displaced due to the mobility of the fiber within the nonwoven, or if the fibers are stretched beyond their elastic limit and are plastically deformed.

Second precursor web 21 can be virtually any web material, the only requirement being that it have sufficient integrity to be formed into the laminate by the process described below. In one embodiment, it can have sufficiently less elongation properties relative to first precursor web 20, such that upon experiencing the strain of fibers from first precursor web 20 being urged out-of-plane in the direction of second precursor web 21, second precursor web 21 will rupture, e.g., by tearing due to extensional failure, such that portions of first precursor web 20 can extend through, (i.e., "punch through" so to speak), second precursor web 21 to form tufts 6 on first side 3 of web 1. In one embodiment second precursor web 21 is a polymer film. Second precursor web 21 can also have sufficient elongation properties to be formed into looped fibers, as described above with respect to first precursor web 20.

Figure 2:
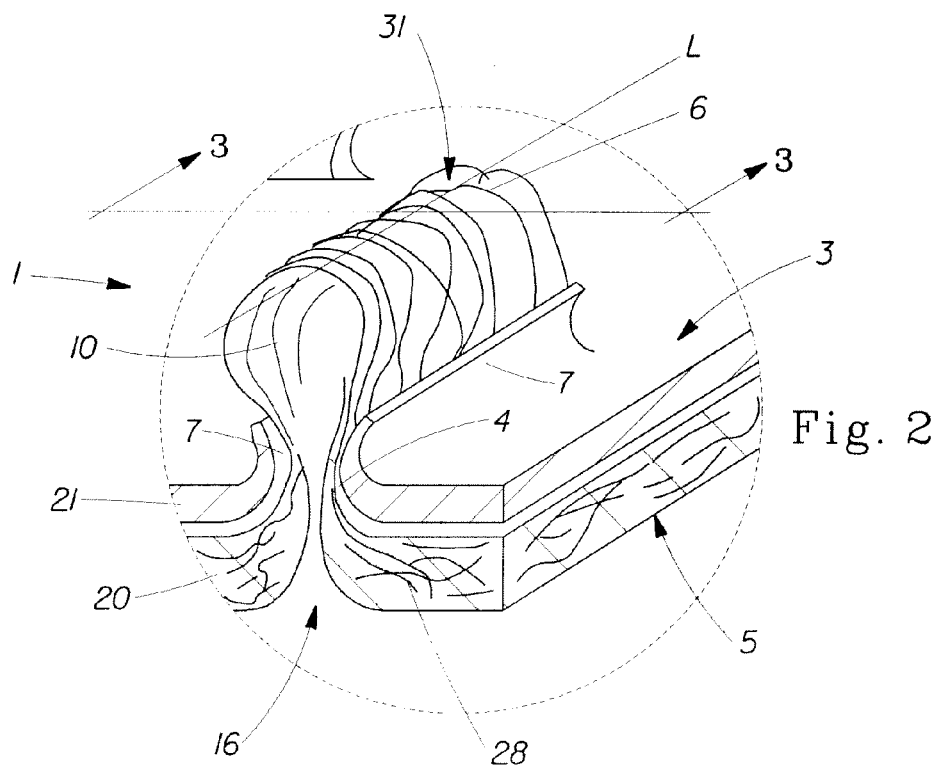
FIG. 2 is an enlarged view of a portion of the web shown in FIG. 1.

A representative tuft 6 for the embodiment of web 1 shown in FIG. 1 (where the second precursor web 21 is "punched through" by first precursor web) is shown in a further enlarged view in FIG. 2. As shown in FIG. 2 or 3, tuft 6 comprises a plurality of looped fibers 8 that are substantially aligned such that tuft 6 has a distinct linear orientation and a longitudinal axis L. Tuft 6 also have a transverse axis T generally is orthogonal to longitudinal axis L in the MD-CD plane. In the embodiment shown in FIGS. 1 and 2, longitudinal axis L is parallel to the MD. In one embodiment, all the spaced apart tufts 6 have generally parallel longitudinal axes L. The number of tufts 6 per unit area of web 1, i.e., the area density of tuft 6, can be varied from 1 tuft per unit area, e.g., square centimeter to as high as 100 tufts per square centimeter. There can be at least 10, or at least 20 tufts 6 per square centimeter, depending on the end use. In general, the area density need not be uniform across the entire area of web 1, but tufts 6 can be only in certain regions of web 1, such as in regions having predetermined shapes, such as lines, stripes, bands, circles, and the like.

As can be appreciated by the description herein, in many embodiments of web 1 openings 4 of second precursor web 21 will have a distinct linear orientation and a longitudinal axis, which is oriented parallel to the longitudinal axis L of its corresponding tuft 6. Likewise, openings 4 will also have a transverse axis generally orthogonal to longitudinal axis in the MD-CD plane.

As shown in FIGS. 1-4, tufts 6 can extend through openings 4 in second precursor web 21. Openings 4 are formed by locally rupturing second precursor web 21 by the process described in detail below. Rupture may involve a simple splitting open of second precursor web 21, such that opening 4 remains a simple two-dimensional aperture. However, for some materials, such as polymer films, portions of second precursor web 21 can be deflected or urged out-of-plane (i.e., the plane of second precursor web 21) to form flap-like structures, referred to herein as flap, or flaps, 7. The form and structure of flaps 7 is highly dependent upon the material properties of second precursor web 21. Flaps 7 can have the general structure of one or more flaps, as shown in FIGS. 1 and 2. In other embodiments, flap 7 can have a more volcano-like structure, as if the tuft 6 is erupting from the flap 7. In other embodiments, flaps 7 can virtually completely cover tufts 6, such that they form a "cap" over tufts 6.

In one embodiment flaps 7 do not contribute significantly to the material of tufts 6, and particularly do not contribute significantly to the tactile quality of tufts 6. In one embodiment, therefore, the laminate web 1 comprises at least two layers (i.e., precursor webs 20 and 21), but at least one of the layers (i.e., precursor web 21 in FIGS. 1-4) does is not significantly affect on the tactile qualities of tufts 6.

In one embodiment, flaps 7 may extend out of plane significantly, even being as high, so to speak, as the tufts 6 themselves. In this embodiment flaps 7 can cause the tufts 6 to be more resilient and less susceptible to flattening due to compressive or bending forces. In one embodiment, therefore, the laminate web 1 comprises at least two layers (i.e., precursor webs 20 and 21), and both layers affect the tactile qualities of tufts 6.

Tufts 6 can comprise looped fibers from both precursor webs. Therefore, tufts 6 can be, in a sense, either "punched through" second precursor web 21 or "pushed into" the tufts of second precursor web 21. In either case, it can be said that first and second precursor webs can be "locked" in place by frictional engagement with openings 4. In some embodiments, for example, the lateral width of opening 4 (i.e., the dimension measured parallel to its transverse axis) can be less than the maximum width of the tooth that formed the opening (per the process described below). This indicates a certain amount of recovery at the opening that tends to constrain tuft 6 from pulling back out through opening 4. The frictional engagement of the tufts and openings provides for a laminate web structure having permanent tufting on one side that can be formed without adhesives or thermal bonding.

Because in some embodiments at least one of the layers (e.g., a relatively low elongation polymer film or tissue paper second precursor web 21 in FIGS. 1-4) does not significantly contribute material to the tufts 6 (such as in the embodiments shown in FIGS. 1-4) a web 1 comprising a nonwoven first precursor web 20 can be characterized as being predominantly fibrous on both sides of web 1 with the fibers being contributed only by nonwoven first precursor web 20. Therefore, tufts 6 can be spaced sufficiently closely so as to effectively cover first side 3 of web 1. In such an embodiment, both sides of web 1 appear to be nonwoven, with a difference between the two sides 3 and 5 being a difference in surface texture. Therefore, in one embodiment, the invention can be described as a laminate material of two or more precursor webs, wherein both sides of the laminate web are substantially covered by fibers from only one of the precursor webs.

As shown in FIGS. 1-4, one characteristic of tufts 6 can be the predominant is directional alignment of the fibers 8 or 18. For example, looped, aligned fibers 8 can be described as having a significant or major vector component parallel to the Z-CD plane and the looped fibers 8 have a substantially uniform alignment with respect to transverse axis T when viewed in plan view, such as in FIG. 4. By "looped" fibers 8 is meant fibers 8 that are integral with and begin and end in first precursor web 20 but extend outwardly in the Z-direction from first surface 13 of second precursor web 21. By "aligned" with respect to looped fibers 8 of tufts 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T.

In contrast, non-looped fibers 18 are integral with, but only begin in first precursor web 20 and have a free end extending outwardly in the Z-direction from first surface 13 of second precursor web 21. Loose fibers 18 can also have a generally uniform alignment described as having a significant or major vector component parallel to the Z-CD plane.

For both looped fibers 8 and loose fibers 18, the alignment is a characteristic of tufts 6 prior to any post-manufacture deformation due to winding onto a roll, or compression in use in an article of manufacture.

Figure 4:
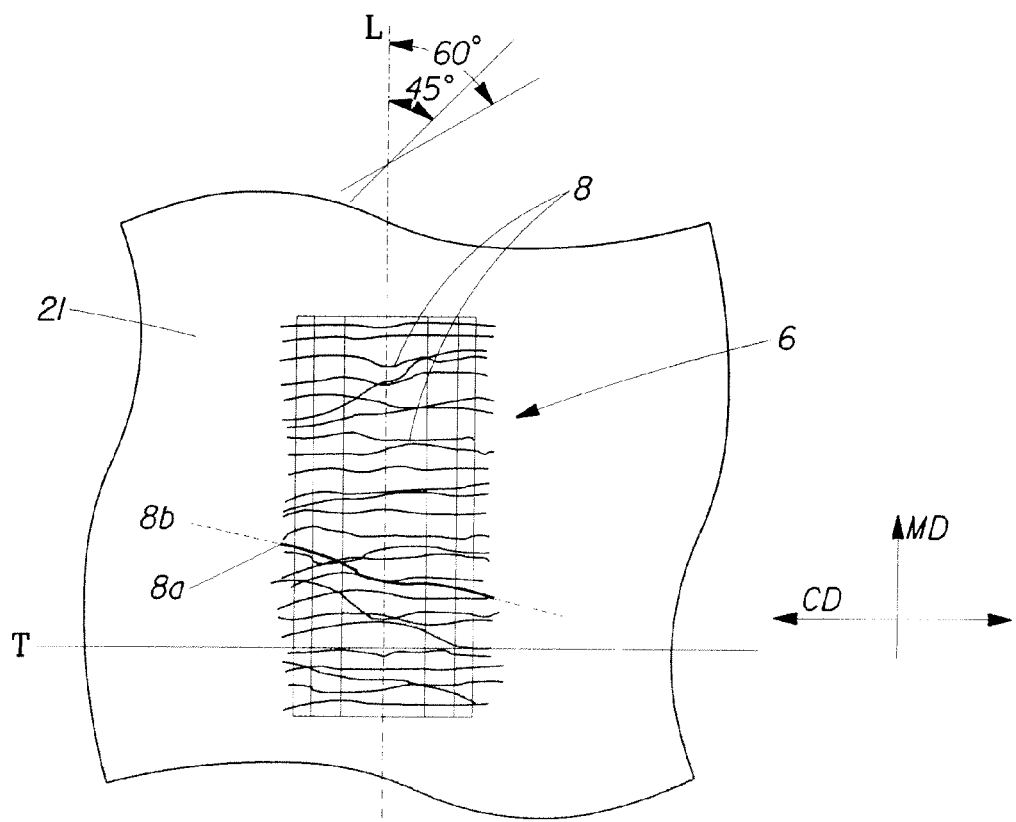
FIG. 4 is a plan view of a portion of the web as indicated by 4-4 in FIG. 3.

As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In a preferred embodiment, at least 50%, more preferably at least 70%, and more preferably at least 90% of fibers 8 of tuft 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for is determining the angle of looped fibers 8 from longitudinal axis L. For example, as shown in FIG. 4, one fiber 8*a* is shown emphasized by a heavy line, and its linear approximation 8*b* is shown as a dashed line. This fiber makes an angle of approximately 80 degrees with the longitudinal axis (measured counterclockwise from L).

The orientation of looped fibers 8 in the tufts 6 is to be contrasted with the fiber composition and orientation for first precursor web 20, which, for nonwoven webs is best described as having a substantially randomly-oriented fiber alignment. In a woven web embodiment, the orientation of the looped fibers 8 in tufts 6 could be the same as described above, but the fibers of first precursor web 20 would have the orientation associated with the particular weaving process used to make the web, e.g., a square weave pattern.

In the embodiment shown in FIG. 1 the longitudinal axes L of tufts 6 are generally aligned in the MD. Tufts 6 and, therefore, longitudinal axes L, can, in principle, be aligned in any orientation with respect to the MD or CD. Therefore, in general, it can be said that for each tuft 6, the looped aligned fibers 8 are aligned generally orthogonal to the longitudinal axis L such that they have a significant vector component parallel to transverse axis T, and more preferably a major vector component parallel to transverse axis T.

In some embodiments, due to the preferred method of forming tufts 6, as described below, another characteristic of tufts 6 comprising predominantly looped, aligned fibers 8, can be their generally open structure characterized by open void area 10 defined interiorly of tufts 6, as shown in FIGS. 2 and 3. The void area 10 may have a shape that is wider or larger at the distal end 31 of the tuft 6 and narrower at the base 17 of the tuft 6. This is opposite to the shape of the tooth which is used to form the tuft 6. By "void area" is not meant an area completely free of any fibers; the term is meant as a general description of the general appearance of tufts 6. Therefore, it may be that in some tufts 6 a loose fiber 18 or a plurality of loose fibers 18 may be present in the void area 10. By "open" void area is meant that the two longitudinal ends of tuft 6 are generally open and free of fibers, such that tuft 6 can form something like a "tunnel" structure in an uncompressed state, as shown in FIG. 3.

Additionally, as a consequence of a preferred method of making web 1, the second side 5 of web 1 exhibits discontinuities 16 characterized by a generally linear indentation defined by formerly random fibers of the second surface 14 of first precursor web 20 having been urged directionally (i.e., in the "Z-direction" generally orthogonal to the MD-CD plane as shown in FIGS. 1 and 3) into tufts 6 by the teeth of the forming structure, described in detail below. The abrupt change of orientation exhibited by the previously randomly-oriented fibers of first precursor web 20 defines the discontinuity 16, which exhibits a linearity such that it can be described as having a longitudinal axis generally parallel to longitudinal axis L of the tuft 6. Due to the nature of many nonwoven webs useful as first precursor webs 20, discontinuity 16 may not be as distinctly noticeable as tufts 6. For this reason, the discontinuities 16 on the second side 5 of web 1 can go unnoticed and may be generally undetected unless web 1 is closely inspected. As such, the second side 5 of web 1 can have the look and feel of an un-tufted first precursor web 20. Thus in some embodiments, web 1 can have the textured look and feel of terry cloth on first side 3, and a relatively smooth, soft look and feel on second side 5, both sides being comprised of fibers from the same nonwoven web, i.e., the first precursor web 20. In other embodiments, discontinuities 16 can appear as apertures, and may be apertures through web 1 via the ends of the tunnel-like tufts 6.

From the description of web 1 comprising a nonwoven first precursor web 20, it can be seen that the fibers 8 or 18 of tuft 6 can originate and extend from either the first surface 12 or the second surface 14 of first precursor web 20. Of course the fibers 8 or 18 of tuft 6 can also extend from the interior 28 of first precursor web 20. As shown in FIG. 3, the fibers 8 or 18 of tufts 6 extend due to having been urged out of the generally two-dimensional plane of first precursor web 20 (i.e., urged in the "Z-direction" as shown in FIG. 3). In general, the fibers 8 or 18 of the tufts 6 comprise fibers that are integral with and extend from the fibers of the first precursor web 20.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the is second precursor web and a plurality of discrete tufts, each of the discrete tufts comprising a plurality of tufted fibers being integral extensions of the first precursor web and extending through second precursor web; and a second side, the second side comprising the first precursor web.

The extension of fibers 8 or 18 can be accompanied by a general reduction in fiber cross sectional dimension (e.g., diameter for round fibers) due to plastic deformation of the fibers and Poisson's ratio effects. Therefore, the aligned looped fibers 8 of tuft 6 can have an average fiber diameter less than the average fiber diameter of the fibers of first precursor web 20. It is believed that this reduction in fiber diameter contributes to the perceived softness of the first side 3 of web 1, a softness that can be comparable to cotton terry cloth, depending on the material properties of the first precursor web 20. It has been found that the reduction in fiber cross-sectional dimension is greatest intermediate the base 17 and the distal portion 31 of tuft 6. This is believed to be due to the preferred method of making, as disclosed more fully below. Briefly, as shown on FIG. 3, it is believed that portions of fibers at the base 17 and distal portion 31 of tufts 6 are adjacent the tip of teeth 110 of roll 104, described more fully below, and are frictionally locked and immobile during processing. Thus, the intermediate portions of tufts 6 are more free to stretch, or elongate, and accordingly, can experience a corresponding fiber cross sectional dimension reduction. Some fibers of first precursor web 20 may laterally squeeze the base 17 of the tuft 6. The base 17 of the tuft 6 may even be closed (if the fibers from the tuft 6 are close enough together to touch) or may remain open. Generally, any opening at the base 17 is narrow. The closing or narrowing or squeezing of other fibers at the base 17 can help to stabilize the tufts 6 and second precursor web 21.

Figure 5:
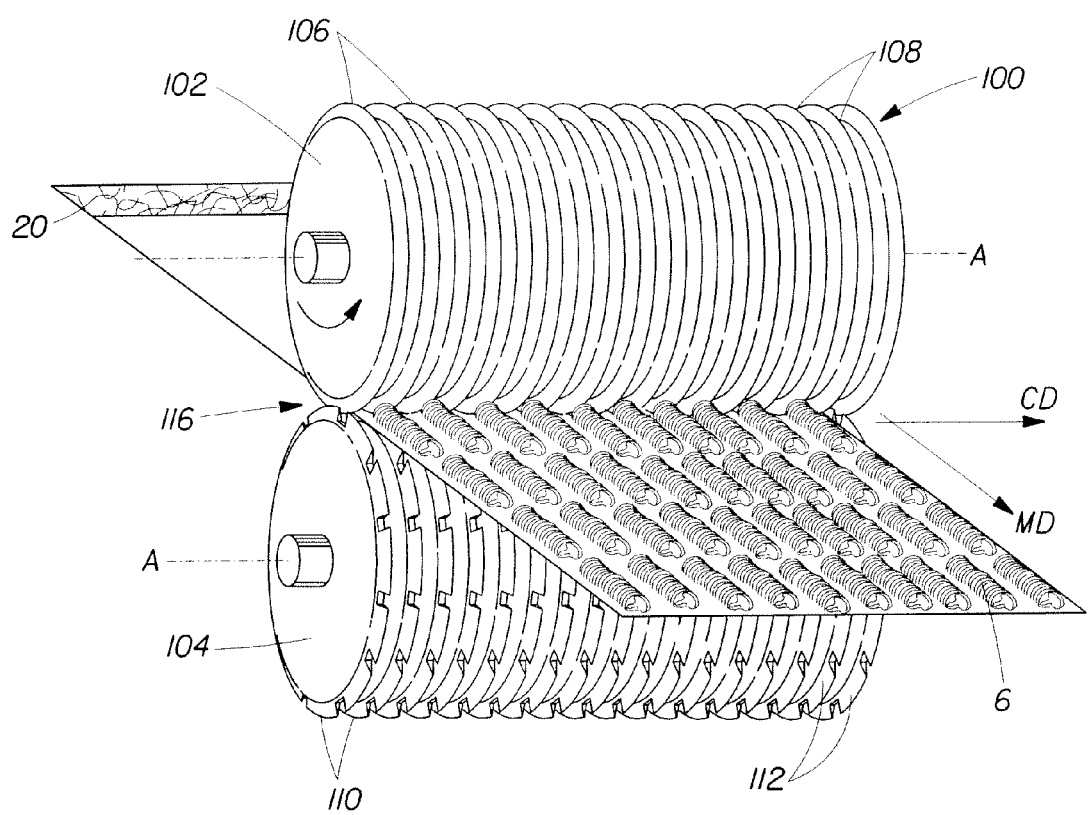
FIG. 5 is a perspective view of an apparatus for forming the web of the present invention.

Referring to FIG. 5 there is shown an apparatus and method for making web 1 of the present invention. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 6, discussed below. Both or either of rolls 102 and 104 can be heated by means known in the art such as by using hot oil filled rollers or electrically-heated rollers.

In FIG. 5, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with tufts 6 protruding from both sides of the web 1. An apparatus could also be designed to have teeth that pointing in opposite directions on the same roll. This would result in a web with tufts 6 being produced on both sides of the web.

The method of making a web 1 of the present invention in a commercially viable continuous process is depicted in FIG. 5. Web 1 is made by mechanically deforming precursor webs, such as first and second precursor webs, 20 and 21 that can each be described as generally planar and two dimensional prior to processing by the apparatus shown in FIG. 5. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process is disclosed in the '801 patent, and the differences are apparent in the respective webs produced thereby. As described below, the teeth 110 of roll 104 have a specific geometry associated with the leading and trailing edges that permit the teeth to essentially "punch" through the precursor webs 20, 21 as opposed to, in essence, deforming the web. In a two layer laminate web 1 the teeth 110 urge fibers from a first precursor web 20 simultaneously out-of-plane and through second precursor web 21, which is punctured, so to speak, by the teeth 110 pushing the fibers 8 through to form tufts 6. Therefore, a web 1 of the present invention can have tufts 6 of loose fiber ends 18 and/or "tunnel-like" tufts 6 of looped, aligned fibers 8 extending through and away from the surface 13 of a first side 3, unlike the "tent-like" rib-like elements of SELF webs which each have continuous side walls associated therewith, i.e., a continuous "transition zone," and which do not exhibit interpenetration of one layer through another layer.

Precursor webs 20 and 21 are provided either directly from their respective web making processes or indirectly from supply rolls (neither shown) and moved in the machine direction to the nip 116 of counter-rotating intermeshing rolls 102 and 104. The precursor webs are preferably held in a sufficient web tension so as to enter the nip 16 in a generally flattened condition by means well known in the art of web handling. As each precursor web 20, 21 goes through the nip 116 the teeth 110 of roll 104 which are intermeshed with grooves 108 of roll 102 simultaneously urge portions of first precursor web 20 out of the plane of first precursor web 20 and through second precursor web 21 to form tufts 6. In effect, teeth 110 "push" or "punch" fibers of first precursor web 20 through second precursor web 21.

As the tip of teeth 110 push through first and second precursor webs 20, 21 the portions of the fibers of first precursor web 20 that are oriented predominantly in the CD across teeth 110 are urged by the teeth 110 out of the plane of first precursor web 20. Fibers can be urged out of plane due to fiber mobility, or they can be urged out of plane by being stretched and/or plastically deformed in the Z-direction. Portions of first precursor web 20 urged out of plane by teeth 110 push through second precursor web 21, which due to its relatively lower extensibility, ruptures, thereby resulting in formation of tufts 6 on first side 3 of web 1. Fibers of first precursor web 20 that are predominantly oriented generally parallel to the longitudinal axis L, i.e., in the MD of precursor web 20 is as shown in FIG. 1, are simply spread apart by teeth 110 and remain substantially in their original, randomly-oriented condition. This is why the looped fibers 8 can exhibit the unique fiber orientation in embodiments such as the one shown in FIGS. 1-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 20, 21 can possess differing material properties with respect to the ability of the precursor webs to elongate before failure, e.g., failure due to tensile stresses. In particular, a nonwoven first precursor web 20 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts. However, in other embodiments, both precursor webs have sufficient elongation such that fibers thereof can move or stretch sufficiently to form tufts 6.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-ofplane tufts. Therefore, in one embodiment, first precursor web 20 can be a nonwoven web having relatively low inter-fiber bonding, and second precursor web 21 can be a non-woven web having relatively high inter-fiber bonding, such that the fibers of first precursor web can extend out of plane, while the fibers of second precursor web 21 cannot. Upon sufficient force applied to first precursor web 21, the fibers therein tend to extend, while the fibers of second precursor web, unable to extend, is tend to break.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20, 21 permits many varied webs 1 to be made for many purposes. For example, web 1 made from a first precursor web 20 comprising a relatively high basis weight woven fabric having MD and CD woven plastically-extensible threads and a second precursor web 21 comprising relatively high basis weight, relatively low-extensible synthetic polymer nonwoven material could be made into a strong, porous ground covering, such as an erosion control device useful for reducing sloping path deterioration and enabling growth of indigenous vegetation in unstable soil.

Figure 6:
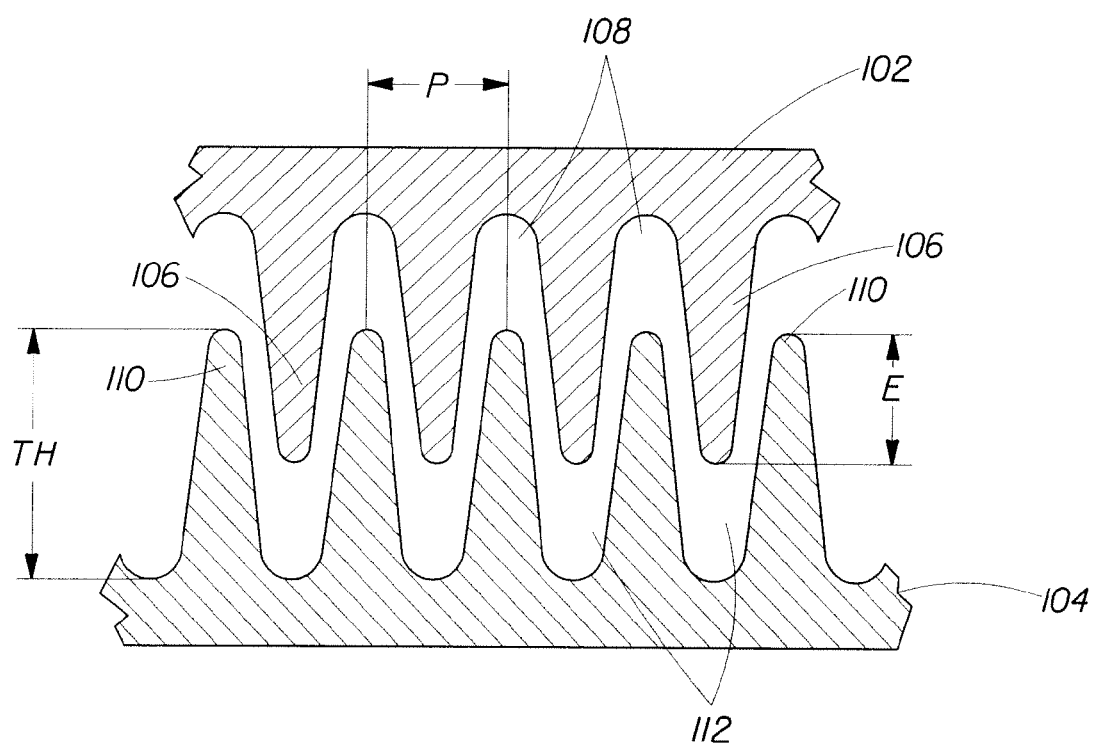
FIG. 6 is a cross-sectional depiction of a portion of the apparatus shown in FIG. 5.

FIG. 6 shows in cross section a portion of the intermeshing rolls 102 and 104 and ridges 106 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor webs 20, 21 and the desired characteristics of web 1. For example, in general, the greater the level of engagement E, the greater the necessary elongation or fiber-to-fiber mobility characteristics the fibers of first precursor web 20 must possess. Also, the greater the density of tufts 6 desired (tufts 6 per unit area of web 1), the smaller the pitch should be, and the smaller the tooth length TL and tooth distance TD should be, as described below.

Figure 7:
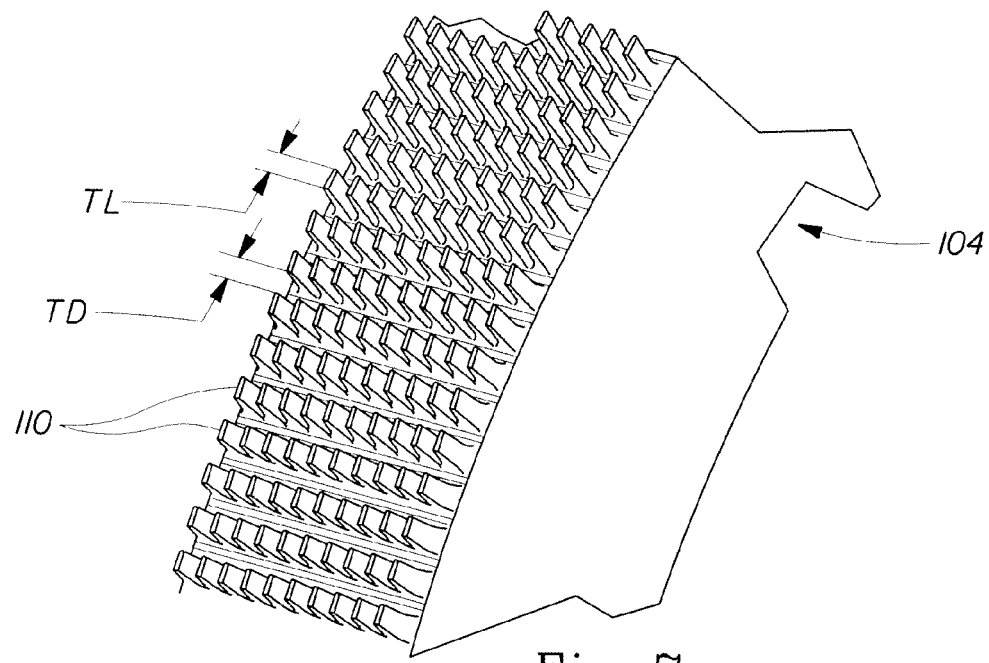
FIG. 7 is a perspective view of a portion of the apparatus for forming one embodiment the web of the present invention.

FIG. 7 shows one embodiment of a roll 104 having a plurality of teeth 110 useful for making a terry cloth-like web 1 from a nonwoven first precursor web 20 having a basis weight of between about 60 gsm and 100 gsm, preferably about 80 gsm and a polyolefinic film (e.g., polyethylene or polypropylene) second precursor web 21 having a density of about 0.91-0.94 and a basis weight of about 20 gsm.

Figure 8:
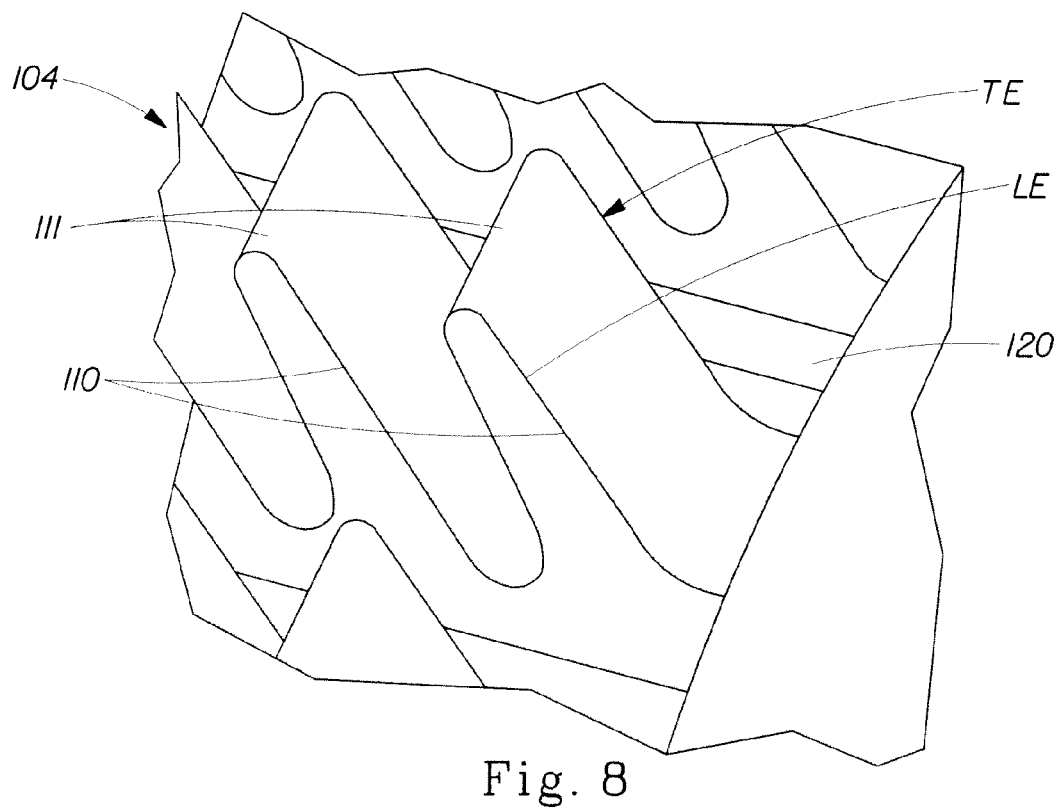
FIG. 8 is an enlarged perspective view of a portion of the apparatus for forming the web of the present invention.
Figure 9:
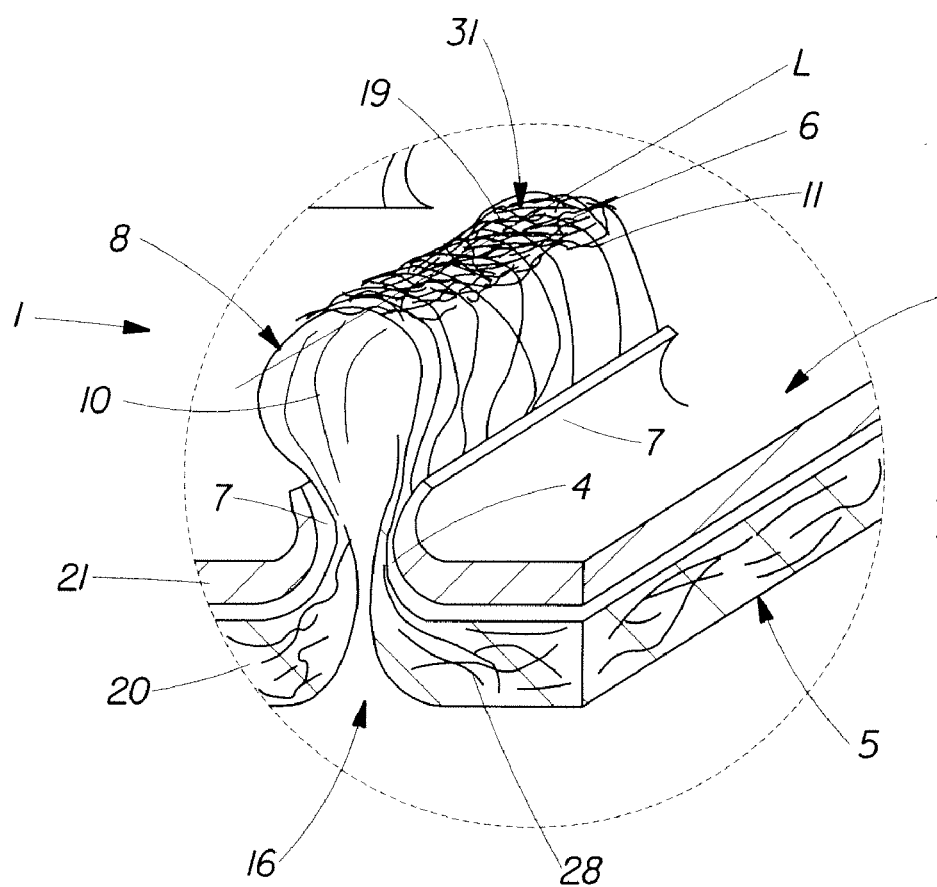
FIG. 9 is an enlarged view of a portion of another embodiment of a web of the present invention.

An enlarged view of teeth 110 is shown in FIG. 8. In this embodiment of roll 104 teeth 110 have a uniform circumferential length dimension TL measured generally from is the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 8, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor webs 20, 21 "cleanly", that is, locally and distinctly, so that the first side 3 of the resulting web 1 can be described as "tufted" rather than "deformed." When so processed, the web 1 is not imparted with any particular elasticity, beyond what the precursor webs 20 and 21 may have possessed originally. The punching through of the precursor web 21 may result in a small portion of the web 21 forming "confetti" or small pieces.

While not wishing to be bound by theory, it is believed that if the fibers of the precursor webs have a highly curvilinear shape, e.g., curled fibers, the resultant tufts 6 will have more looped fibers 8 and less broken fibers 18 as compared to more linear fiber conformations. It is believed that such fiber conformations have a lesser chance of bridging between two adjacent teeth, and, as a result they are less prone to be stretched is beyond their breaking point, and thus have a greater chance of forming complete loop structures. Furthermore, such curvilinear-shaped fibers can be made by using eccentric bicomponent fibers, or side-by-side bicomponent fibers, such as bicomponent fibers consisting of polyethylene and nylon.

In preferred embodiments first and second precursor webs are nonwoven webs in which there are minimal fiber-to-fiber bonds. For example, the precursor web can be a nonwoven web having a pattern of discrete thermal point bonds, as is commonly known in the art for nonwoven webs. In general, however, it is desirable to minimize the number of bond points and maximize the spacing so as to allow for maximum fiber mobility and dislocation at during formation of tufts 6. In general, utilizing fibers having relatively high diameters, and/or relatively high extension to break, and/or relatively high fiber mobility, results in better and more distinctly formed tufts 6.

Although web 1 is disclosed in preferred embodiments as a two layer web made from two precursor webs, it is not necessary that it be limited to two layers. For example, a three-layer or more laminate can be made from three precursor webs, as long as one of the precursor webs can extend and push through openings in another layer to form tufts. For example, web 1 could comprise the top sheet, secondary topsheet, and core of hygiene products. In general, it is not necessary that adhesive or other bonding means be utilized to make laminate web 1.

The constituent layers of web 1 (e.g., precursor webs 20 and 21 and any other layers) can be held in a face-to-face laminated relationship by virtue of the "locking" effect of the tufts 6 that extend through openings 4 in second precursor web 21. In some embodiments it may be desirable to use adhesives or thermal bonding or other bonding means, depending on the end use application of web 1. For example, a web 1 comprising bicomponent fiber nonwoven webs can be through-air bonded after formation of tufts 6 to provide for layer-to-layer adhesion for greater peel strength. Additionally, it may be desirable to apply adhesive to at least a portion of one of the precursor webs. For example, in some embodiments adhesive, chemical bonding, resin or powder bonding, or thermal bonding between layers can be selectively applied to certain regions or all of the precursor webs. In the case of adhesive application, for example, adhesive can be applied is in a continuous manner, such as by slot coating, or in a discontinuous manner, such as by spraying, extruding, and the like. Discontinuous application of adhesive can be in the form of stripes, bands, droplets, and the like.

In a multilayer web 1 each precursor web can have different material properties, thereby providing web 1 with beneficial properties when used as a topsheet in a disposable absorbent article such as a sanitary napkin. For example, web 1 comprising two (or more) precursor webs, e.g., first and second precursor webs, can have beneficial fluid handling properties. For superior fluid handling, for example, first precursor web 20 can be comprised of relatively hydrophilic fibers. Second precursor web 21 can be comprised of relatively hydrophobic fibers. The tufts 6 of such a web could form a topsheet having a relatively hydrophobic body-facing surface, with hydrophilic tufts to pull fluid away from the body and through the topsheet. Fluid deposited upon the upper, relatively hydrophilic tufts can be quickly transported away from the relatively hydrophobic layer to the portion of the article underlying the second precursor web layer (e.g., the absorbent core). Without being bound by theory, it is believed that one reason for the observed rapid fluid transport is the capillary structures formed by the generally aligned fibers 8, 18 of tufts 6. The fibers 8, 18 form directionally-aligned capillaries between adjacent fibers, and the capillary action is enhanced by the general convergence of fibers near the base 17 of tufts 6.

It is believed that the rapid fluid transport is further increased due to the ability of fluid to enter the web 1 via the voids 10 defined by looped tufts 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics.

Figure 10:
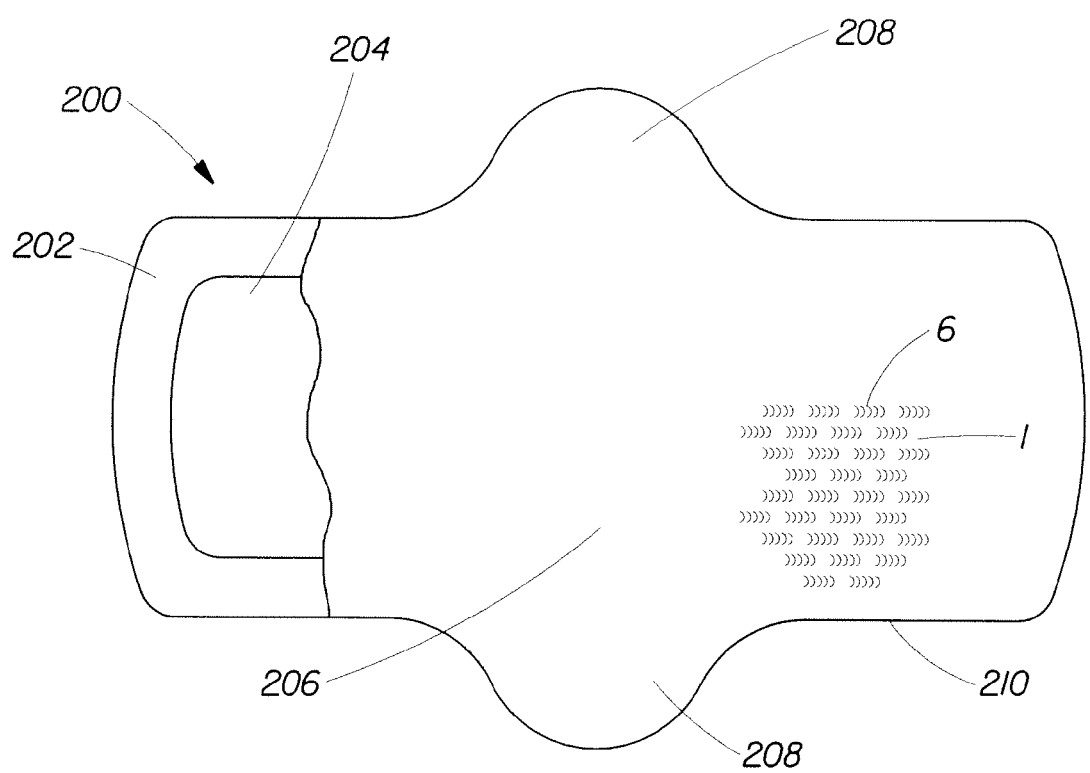
FIG. 10 is a partial cut away plan view of a sanitary napkin of the present invention.

FIG. 10 shows in partial cut away plan view a sanitary napkin having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. Sanitary napkin 1 can have side extensions, commonly referred to as "wings" 208 designed to wrap the sides of the crotch region of the panties of the user of sanitary napkin 1. Sanitary is napkins, including topsheets for use as the body facing surface thereof, are well known in the art and need no detailed description of various alternative and optional designs. In addition to sanitary napkins, web 1 can also be used in a diaper or adult incontinence product or other disposable hygiene products. However, it is noted that web 1 can be used as, or as a component of, one or more of a backsheet, core material, topsheet, secondary topsheet, or wing material. Web 1 can also have multiple layers and comprise a topsheet, secondary topsheet, core, backsheet, or any number of layers.

Web 1 is especially useful as a topsheet 206 of sanitary napkin 200. Web 1 is particularly beneficial as a topsheet 206 for sanitary napkins due to the combination of excellent fluid acquisition and distribution to the absorbent core 204, and excellent prevention of rewet to the body-facing surface of topsheet 206 when in use. Rewet can be a result of at least two causes: (1) squeezing out of the absorbed fluid due to pressure on the sanitary napkin 200; and/or (2) wetness entrapped within or on the topsheet 206. In a preferred topsheet 206 both properties, fluid acquisition and fluid retention, are maximized and rewet is minimized. Said differently, preferably a topsheet will exhibit high rates of fluid acquisition, and low levels of rewet.

A topsheet 206 can be made by using a nonwoven first precursor web 20 and a fluid impermeable polyethylene film second precursor web 21. The basis weights of the component webs can be varied, however, in general due to cost and benefit considerations a total basis weight of between about 20 gsm and 80 gsm is desirable for web 1. When a sanitary napkin is used having a topsheet 206 comprising web 1 with first side 3 being the body-facing side, and the second side 5 being in fluid communication with an underlying absorbent core, fluid can be acquired by tufts 6 on first side 3 of web 1 and wicked through second precursor web 21 to second side 5 of web 1 which can then be desorbed to the absorbent core 204. Because tufts 6 are discrete and spaced apart, and are separated by a fluid impermeable second precursor web 21, rewet can be minimized Alternatively, web 1 could be used with first side 3 being the fluid communication side and second side 5 being the body-facing side. This enables the discontinuities 16 to potentially allow fluid to be transported into or through the tufts 6.

In a sanitary napkin of the present invention, topsheet 206 has applied thereto a semi-solid lotion composition. The lotion composition can be any of known lotions, such as lotions comprising petrolatum, which can provide a skin benefit to the user. In a preferred embodiment, the lotion also provides a clean body benefit to the user. That is, the lotion preferably coats the body and renders menses less susceptible to sticking to the body, including hair and skin. Preferably, therefore, the lotion is hydrophobic, and renders hair and skin hydrophobic.

Lotion can be applied in any manner known in the art for applying lotions to nonwoven webs. Lotion can be applied to the tips (i.e., the distal ends) of tufts 6. It has been found that applying lotion to the tips enables efficient transfer to the skin of the wearer. Without being bound by theory, it is believed that the tufts act as little brushes to wipe the lotion onto the body during motion, such as walking.

The lotion of the present invention can include those disclosed in U.S. Pat. Nos. 5,968,025; 6,627,787; 6,498,284; 6,426,444; 6,586,652; 3,489,148; 6,503,526; 6,287,581; 6,475,197; 6,506,394; 6,503,524; 6,626,961; 6,149,934; 6,515,029; 6,534,074; 6,149,932 WO 2000038747; or EP-A 927,050.

In addition to (or instead of) lotion treatments, the topsheet 206 (or portions thereof) can be treated with other materials or compositions to render it sufficiently hydrophobic. For example, the topsheet can be treated with silicone treatments, low surface energy treatments, fluorinated hydrocarbon treatments. In general, relatively hydrophobic means a material or composition having a contact angle with water of at least about 70 degrees, preferably at least about 90 degrees. In general, low surface energy means between about 20 and about 60 dynes per square centimeter, preferably from about 20 to about 50 dynes per square centimeter, and more preferably from about 20-40 dynes per square centimeter.

In a preferred embodiment, web 1 is used as a topsheet 206 in conjunction with a high capacity and highly absorbent core 204. In general, a preferred absorbent core is an airlaid core of the type disclosed in U.S. Pat. Nos. 5,445,777; or 5,607,414. In a preferred embodiment, absorbent core 204 is the type generally referred to as HIPE foams, such as those disclosed in U.S. Pat. Nos. 5,550,167; 5,387,207; 5,352,711; and 5,331, 015. In a is preferred embodiment, absorbent core 204 has a capacity after desorption at 30 cm of less than about 10% of its free absorbent capacity; a capillary absorption pressure of from about 3 to about 20 cm; a capillary desorption pressure of from about 8 to about 25 cm; a resistance to compression deflection of from about 5 to about 85% when measured under a confining pressure of 0.74 psi; and a free absorbent capacity of from about 4 to 125 grams/gram. Each of these parameters can be determined as set forth in U.S. Pat. No. 5,550,167. issued Aug. 27, 1996 to DesMarais. One advantage of utilizing the airlaid or HIPE foam cores as disclosed is that the absorbent core can be made very thin. For example, an absorbent core of the present invention can have an average caliper (thickness) of less than about 20 mm, preferably less than about 10 mm, and the thickness can be less than about 5 mm.

As can be understood from the above description of webs 1 and apparatus 100 of the present invention, many various structures of webs 1 can be made without departing from the scope of the present invention as claimed in the appended claims. For example, topsheet 206 can additionally be coated or treated with medicaments, cleaning fluids, anti-bacterial solutions, emulsions, fragrances, or surfactants. Likewise, apparatus 100 can be configured to only form tufts 6 on a portion of the web 1, or to form varying sizes or area densities of tufts 6.

Another advantage of the process described to produce the webs of the present invention is that the webs can be produced in-line with other web production equipment or in-line with disposable absorbent article production equipment. Additionally, there may be other solid state formation processes that can be used either prior to or after the process of the present invention. For example, a web could be processed according to the present invention and then apertured with a stretching process, such as one described in U.S. Pat. No. 5,658,639 to Curro et al. Alternatively, a material could be made into a composite through a variety of processes, such as one described in US Publication No. 2003/028,165A1 to Curro et al. or ring rolled, for example as in U.S. Pat. No. 5,167,897 to Weber et al. and then processed according to the present invention. The resulting webs can thus exhibit the combined benefits of these multiple material modifications.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet comprising:
      a) a first web comprising a nonwoven layer; and
      b) a second web disposed over said nonwoven layer and at least partially defining said body-facing said, said second web comprising:
         i) a plurality of openings;
         ii) a plurality of apertures that are separate and distinct from said plurality of openings; and
         iii) a discrete tuft of fibers extending from said nonwoven layer and through said openings;
   a lotion composition applied to at least a portion of said body-facing side of said topsheet;
   a backsheet; and
   an absorbent core in fluid communication with said topsheet, said absorbent core positioned between said nonwoven layer and said backsheet.

2. The absorbent article of claim 1, wherein said lotion is applied to said topsheet in plurality of spaced apart stripes.

3. The absorbent article of claim 1, wherein said second web is a film-based web.

4. The absorbent article of claim 1, wherein said second web is a nonwoven web.

5. The absorbent article of claim 1, wherein said discrete tufts of fibers comprise a plurality of looped fibers.

6. The absorbent article of claim 1, wherein said lotion comprises petrolatum.

7. The absorbent article of claim 1, wherein said lotion is hydrophobic.

8. The absorbent article of claim 1, wherein said lotion is semi-solid.

9. The absorbent article of claim 1, wherein said topsheet further comprises a low surface energy treatment so that a portion of said topsheet comprising said treatment has a surface energy of between about 20 and about 60 dynes per square centimeter.

10. An absorbent article comprising:
   a topsheet having a body-facing side and comprising a plurality of discrete tufts of fibrous material,
   a backsheet; and
   an absorbent core disposed between said topsheet and said backsheet, said absorbent core being in fluid communication with said topsheet, said absorbent core having an average thickness of less than about 10 mm, and a free absorbent capacity of from about 4 to about 125 grams per gram;
   wherein said topsheet comprises a first web and a second web, wherein said first web comprises a nonwoven web, wherein said second web comprises a film, wherein said tufts comprise fibers of said first web that integrally extend from said first web and through said second web, and wherein discrete portions of said film are urged out of plane and form a cap or cover over said tufts; and
   wherein said topsheet comprises a lotion.

* * * * *

UNITED STATES PATENT AND TRADEMARK OFFICE
CERTIFICATE OF CORRECTION

| | |
|---|---|
| PATENT NO. | : 7,910,195 B2 |
| APPLICATION NO. | : 12/778478 |
| DATED | : March 22, 2011 |
| INVENTOR(S) | : John Lee Hammons et al. |

It is certified that error appears in the above-identified patent and that said Letters Patent is hereby corrected as shown below:

Column 1

Line 20, delete "is".

Column 3

Line 3, delete "is".

Column 5

Line 36, delete "is".

Line 64, delete "s".

Column 6

Line 12, delete "is".

Line 56, delete "is".

Column 7

Line 30, delete "is".

Column 8

Line 6, delete "is".

Line 49, delete "is".

Column 9

Line 22, delete "is".

Column 10

Line 38, delete "is".

Column 11

Line 57, delete "is".

Column 12

Line 34, delete "is".

Signed and Sealed this
Twenty-eighth Day of February, 2012

David J. Kappos
*Director of the United States Patent and Trademark Office*

Column 13

Line 9, delete "is".

Line 52, delete "is".

Column 15

Line 6, delete "is".

Line 50, delete "is".

Column 17

Line 1, delete "is".